United States Patent [19]

Elbe et al.

[11] Patent Number: 5,622,546
[45] Date of Patent: Apr. 22, 1997

[54] MOULD-RESISTANT EMULSION PAINTS

[75] Inventors: Hans-Ludwig Elbe, Wuppertal; Wilfried Paulus; Heinrich Schrage, both of Krefeld; Martin Kugler, Leichlingen; Franz Kunisch, Odenthal, all of Germany

[73] Assignee: Bayer Aktiengesellschaft, Leverkusen, Germany

[21] Appl. No.: 596,163

[22] PCT Filed: Aug. 8, 1994

[86] PCT No.: PCT/EP94/02627

§ 371 Date: Feb. 14, 1996

§ 102(e) Date: Feb. 14, 1996

[87] PCT Pub. No.: WO95/06091

PCT Pub. Date: Mar. 2, 1995

[30] Foreign Application Priority Data

Aug. 20, 1993 [DE] Germany ............................ 43 28 074.9

[51] Int. Cl.⁶ .......................... A01N 43/10; C07D 333/50
[52] U.S. Cl. ...................... 106/18.33; 504/289; 514/443; 514/448; 549/43

[58] Field of Search .................. 106/15.05, 18.32, 106/18.33; 514/443, 448; 504/289; 549/43

[56] References Cited

U.S. PATENT DOCUMENTS

| 4,663,347 | 5/1987 | Atkinson et al. | 548/251 |
| 5,118,680 | 6/1992 | Muller et al. | 514/324 |
| 5,244,893 | 9/1993 | Elbe et al. | 514/212 |

FOREIGN PATENT DOCUMENTS

| 146243 | 10/1984 | European Pat. Off. . | |
| 160408 | 11/1985 | European Pat. Off. | 549/53 |
| 512349 | 11/1992 | European Pat. Off. . | |
| 526951 | 2/1993 | European Pat. Off. . | |
| 3832846 | 9/1988 | Germany . | |
| 3832848 | 3/1990 | Germany | 549/53 |
| 2193961 | 8/1987 | United Kingdom . | |

Primary Examiner—Anthony Green
Attorney, Agent, or Firm—Sprung Horn Kramer & Woods

[57] ABSTRACT

The application relates to emulsion paints which are protected against fungal infestation by the use of N-alkyl-benzothiophene-2-carboxamide S,S-dioxides.

1 Claim, No Drawings

MOULD-RESISTANT EMULSION PAINTS

The invention relates to mould-resistant emulsion paints which contain as fungicide N-alkyl- preferably N-cyclohexyl-benzothiophene-2-carboxamide S,S-dioxide and which remain free from fungus and stable in colour permanently, i.e. even after exposure in warm ambient air and humidity (condensation or rain) or after thermal stress.

Benzothiophene-2-carboxamide S,S-dioxides (BCD's), a process for their preparation and their fungicidal action are known (DE-A-41 15 184). A description is given in particular of their activity against phytopathogenic fungi and dematophytes. It is also stated that BCD's are suitable for the protection of industrial materials against microbial alteration or destruction. Among the industrial materials mentioned are coating compositions. The majority of the BCD's described, however, when in alkaline media, for example in emulsion paints, undergo hydrolysis to liberate aniline derivatives, which are known to have a strong tendency towards autoxidation, a process in which they become discoloured, so that these BCD's cannot be considered for use as paint fungicides in emulsion paints.

Suprisingly it has now been found that there are substances among the BCD's whose spectrum of action is so wide that it covers not only phytopathogenic fungi and dermatophytes but also the mould fungi which commonly grow on coatings. These compounds are, surprisingly, also so stable to hydrolysis and stable in colour that they are outstandingly suited to the production of mould-resistant emulsion paints. The application therefore relates to emulsion paints comprising N-alkyl-benzothiophene-2-carboxamide S,S-dioxides. Preferred N-alkyl compounds are those in which alkyl represents methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, n- or i-octadecyl, or represents allyl, n- or i-nonyl, n- or i-decyl, n- or i-dodecyl, n- or i-octadecyl, or represents allyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl; and additionally represents cyclopropyl, cyclopropylmethyl, cyclopropylethyl, cyclopropylpropyl, cyclopentyl, cyclopentylmethyl, cyclopentylethyl, cyclopentylpropyl, cyclohexyl, cyclohexylmethyl, cyclohexylethyl or cyclohexylpropyl, each of which is optionally substituted from one to four times in the cycloalkyl moiety by identical or different substituents consisting of fluorine, chlorine, bromine, methyl, ethyl, n- or i-propyl, chloromethyl, dichloromethyl or trifluoromethyl.

Particular preference is given to N-n-butyl-, N-n-pentyl-, N-n-hexyl-, N-cyclo-hexylmethyl-, N-cyclohexyl-benzothiophene-2-carboxamide S,S-dioxides.

Very particular preference is given to N-cyclohexyl-benzothiophene-2-carboxamide S,S-dioxide.

These compounds are distinguished by high thermal stability so that, unlike the other BCD's and other common commercial fungicides, they can be used without a loss in action in emulsion paints including those which are used for coating heat insulation panels, the coated panels being passed through a drying tunnel and exposed to relatively high temperatures.

The emulsion paints contain the paint fungicides which can be used in accordance with the invention, in this context, in quantities of 0.05–5%, preferably of 0.2–2%, based on film weight.

The paint fungicides which can be used in accordance with the invention are employed in emulsion paints both alone and together with other active ingredients, for example together with preservatives in order to ensure the stability of the emulsion paints on storage, but also together with other fungicides and/or algicides, insecticides, molluscicides.

By means of these combinations of active ingredients, the spectrum of action of the N-alkyl-benzothiophene-2-carboxamide S,S-dioxides is enlarged still further, or particular effects are achieved. In many cases, synergistic effects are obtained. If the combinations of active ingredient are present in specific weight ratios, the synergistic effect is evident with particular clarity. However, the weight ratios of the active ingredients in the combinations of active ingredients can be varied within a relatively large range.

In this context, preferred co-components are:
Triazoles:
  amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, metconazole, epoxyconazole, paclobutrazol, penconazole, propioconazole, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and the metal salts and acid adducts thereof.
Imidazoles:
  imazalil, pefurazoate, prochloraz, triflumizole, 2-(1-tert-butyl)-1-(2-chlorophenyl)-3-(1,2,4-triazol-l-yl)-propan-2-ol, thiazole carboxanilides such as 2',6'-dibromo-2-methyl-4-trifluoromethoxy-4'-trifluoromethyl- 1,3-thiazole-5-carboxanilides and the metal salts and acid adducts thereof.

Methyl(E)-2-[2-[6-(2-cyanophenoxy)pyrimidin-4-yloxy]phenyl]3-methoxyacrylate, methyl(E)-2-[2-[6-(2-thioamidophenoxy)pyrimidin-4-yloxy]phenyl]-3-methoxyacrylate, methyl(E)-2-[2-[6-(2-fluorophenoxy)pyrimidin-4-yloxy]phenyl]-3-methoxyacrylate,methyl(E)-2-[2-[6-(2,6-difluorophenoxy)pyrimidin-4-yloxy]phenyl]-3-methoxyacrylate,methyl(E)-2-[2-[3-(pyrimidin-2-yloxy)yloxy)phenoxy]phenyl]-3-methoxyacrylate, methyl(E)-2-[2-[3-(5-methylpyrimidin-2-yloxy)-phenoxy]phenyl]3-methoxyacrylate, methyl(E)-2-[2-[3-(phenyl-sulfonyloxy)phenoxy]phenyl]-3methoxyacrylate, methyl(E)-2-[2-[3-(4-nitrophenoxy)phenoxy]phenyl]-3-methoxy-acrylatemethyl(E)-2-[2-phenoxyphenyl]-3-methoxyacrylate, methyl (E)-2-[2-(3,5-dimethylbenzoyl)pyrrol-1-yl]-3-methoxyacrylate, methyl(E)-2-[2-(3-methoxyphenoxy)phenyl ]-3-methoxyacrylate,methyl(E)-2-[2-(2-phenylethen-1-yl)-phenyl]3-methoxyacrylate, methyl(E-2-[2-(3,5-dichlorophenoxy)pyridin-3-yl]-3-methoxyacrylate, methyl(E)-2-(2-(3-(1,1,2,2-tetrafluoroethoxy)phenoxy)phenyl)-3-methoxyacrylate, methyl(E)-2-(2-[3-alphahydroxybenzyl)phenoxy]phenyl)-3-methoxyacrylate, methyl(E)-2-(2(4-phenoxypyridin-2-yloxy)phenyl)-3-methoxyacrylate, methyl(E)-2-[2-(3-n-propyloxyphenoxy)phenyl]3-methoxyacrylate, methyl (E-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl(E)-2-[2-(3-ethoxyphenoxy)phenyl]-3-methoxyacrylate, methyl(E)-2-[2-(4-tert.-butylpyridin-2-yloxy)phenyl]-3methoxyacrylate, methyl(E)-2-[2-[3-(3-cyanophenoxy)phenoxy]phenyl]-3-methoxyacrylate, methyl(E)-2-[2-(3-methylpyridin-2-yloxymethyl)phenyl]-3- methoxyacrylate, methyl(E)-2-[2-[6-(2-methylphenoxy)pyrimidin-4-yloxy]phenyl]-3methoxyacrylate, methyl(E)-2-[2-(5-bromopyridin-2-yloxymethyl) phenyl]-3-methoxyacrylate, methyl(E)-2-[2-(3-(3-iodopyridin-2-yloxy)phenoxy)phenyl]-3-methoxyacrylate, methyl(E)-2-[2[6-(2-chloropyridin-3-yloxy) pyrimidin-4-yloxy]phenyl]-3methoxyacrylate, (E),(E)methyl-2-[2-(5,6-dimethylpyrazin-2-ylmethyloximinomethyl)phenyl]-3-methoxyacrylate, (E)-methyl-2-{2-[6-(6-methylpyridin-2-yloxy)pyrimidin-4-yloxy]phenyl}-3-methoxyacrylate, E,(E) methyl-2-{2-(3methoxyphenyl)methyloximinomethyl]phenyl}-3-methoxyacrylate, (E)methyl-2-{2(6-(2-azidophenoxy)-pyrimidin-4-yloxy]phenyl}3-methoxyacrylate, (E),(E) methyl2-{2-[6-phenylpyrimidin-4-yl)-methyloximinomethyl]phenyl}-3-methoxyacrylate, (E),(E)-methyl-2-{2-[(4-chlorophenyl)-methyloximinomethyl]phenyl}-3-methoxyacrylate, (E)methyl-2-{2-[6-(2-n-propylphenoxy)-1,3,5-triazin-4-yloxy]phenyl }-3methoxyacrylate (E),(E)methyl-2-{2-[(3-nitrophenyl)methyloximinomethyl]-phenyl}-3-methoxyacrylate;

Succinate dehydrogenase inhibitors such as:

fenfuram, furcarbanil, cyclafluramid, furmecyclox, Seedvax, metsulfovax, pyrocarbolid, oxycarboxin, shirlan, mebenil (mepronil), benodanil, flutolanil (Moncut);

Naphthalene derivatives such as:

terbinafine, naftifine, butenafine, 3-chloro-7-(2-aza-2,7,7-trimethyl-oct-3-en-5-ine); sulphenamides such as dichlofluanid, tolylfluanid, folpet, fluorfolpet; captan, captofol; benzimidazoles such as carbendazim, benomyl, furathiocarb, fuberidazole, thiophonate-methyl, thiabendazole or salts thereof;

Morpholine derivatives such as tridemorph, fenpropimorph, falimorph, dimethomorph, dodemorph; aldimorph, fenpropidin and salts thereof with arylsulfonic acids, for example p-toluenesulphonic acid and p-dodecylphenyl-sulphonic acid;

Dithiocarbamates, cufraneb, ferbam, mancopper, mancozeb, maneb, metam, metiram, thiram zeneb, ziram:

Benzothiazoles such as 2-mercaptobenzothiazole;

benzaxnides such as 2,6-dichloro-N-(4-trifluoromethylbenzyl)-benzamides;

boron compounds such as boric acid, boric esters, borax; formaldehyde and formaldehyde-donor compounds such as benzyl alcohol mono- (poly)-hemiformal, oxazolidines, hexa-hydro-S-triazines, N-methylolchloroacetamide, paraformadehyde, nitropyrine, oxolinic acid, tecloftalam;

tris-N-(cyclohexyldiazeniumdioxy)-aluminium, N-(cyclo-hexyldiazeniumdioxy)-tributyltin and K salts, bis-N-(cyclohexyldiazeniumdioxy)-copper.

N-Methylisothiazolin-3-one, 5-chloro-N-methylisothiazolin-3-one, 4,5-dichloro-N-octyl-isothiazolin-3-one, N-octyl-isothiazolin-3-one, 4,5-trimethylene-isothiazolinones, 4,5-benzisothiazolinones, N-methylolchloroacetamide;

Aldehydes such as cinnamaldehyde, formaldehyde, glutaraldehyde, β-bromocinnamaldehyde; thiocyanates such as thiocyanatomethylthiobenzothiazole, methylene bisthiocyanate, etc.; quaternary ammonium compounds such as benzyldimethyltetradecylammonium chloride, benzyldimethyldodecylammonium chloride, didecyldimethaylammonium chloride;

Iodine derivatives such as diiodomethyl p-tolyl sulphone, 3-iodo-2-propinyl alcohol, 4-chlorophenyl-3-iodopropargyl formal, 3-bromo-2,3-diido-2-propenyl ethylcarbamate, 2,3,3-triiodoallyl alcohol, 3-bromo-2,3-diido-2-propenyl alcohol, 3-iodo-2-propinyl n-butylcarbamate, 3-iodo-2-propinyl n-hexylcarbamate, 3-iodo-2-propinyl cyclohexylcarbamate, 3-iodo-2-propinyl phenylcarbamate;

Phenol derivatives such as tribromophenol, tetrachlorophenol, 3-methyl-4-chlorophenol, 3,5-dimethyl-4-chlorophenol, phenoxyethanol, dichlorphen, o-phenylphenol, m-phenylphenol, p-phenylphenol, 2-benzyl-4-chlorophenol and the alkali metal and alkaline earth metal salts thereof.

Microbicides having an activated halogen group, such as chloroacetamide, bronopol, bronidox, tectamers such as 2-bromo-2-nitro-1,3-propanediol, 2-bromo-4'-hydroxy-acetophenone, 2,2-dibromo-3-nitrile-propionamide, 1,2-dibromo-2,4-dicyanobutane, β-bromo-β-nitrostyrene;

Pyridines such as 1-hydroxy-2-pyridinethione (and their Na, Fe, Mn, Zn salts), tetrachloro-4-methylsulphonylpyridine, pyrimethanol, mepanipyrim, dipyrithion;

Metal soaps such as tin, copper and zinc naphtenate, octoate, 2-ethylhexanoate, oleate, phosphate, benzoate;

Metal salts such as copper hydroxycarbonate, sodium dichromate, potassium dichromate, potassium chromate, copper sulphate, copper chloride, copper borate, zinc fiuorosilicate, copper fiuorosilicate.

Oxides such as tributyltin oxide, $Cu_2O$, CuO, ZnO;

dialkyldithiocarbamates, such as Na salts and Zn salts of dialkyldithiocarbamates, tetramethylthiuram disulphide, potassium N-methyl-dithiocarbamate;

Nitrilessuchas2,4,5,6-tetrachloroisophthalodinitrile, disodium cyano-dithioimidocarbamate;

quinolines such as 8-hydroxyquinoline and the Cu salts thereof;

mucochloric acid, 5-hydroxy-2(5H)-furanone;

4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazin-2-thione, N-(2-p-chlorobenzoylethyl)-hexaminium chloride, potassium N-hydroxym methyl -N'-methy 1-dithiocarbamate, 2-oxo-2-(4-hydroxy-phenyl)acethydroximic acid chloride, phenyl (2-chloro-cyano-vinyl) sulphone, phenyl 1,2-dichloro-2-cyano-vinyl sulphone;

Ag, Zn or Cu-containing zeolites alone or enclosed in polymeric active ingredients;

Very particularly preferred mixtures are those with azaconazole, bromuconazole, cyproconazole, dichlobutrazol, diniconazole, hexaconazole, metaconazole, penconazole, propiconazole, tebuconazole, methyl (E)methoximino[α-(o-tolyloxy)-o-tolyl)]acetate, methyl-(E)-2-{2-[6-(2-cyanophenoxy)-pyrimidin-4-yloxy]phenyl}-3-methoxyacrylate, methfuroxam, carboxin, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, benzisothiazolinones, N-(2-hydroxypropyl)-aminomethanol, benzyl alcohol (hemi)-formal, glutaraldehyde, omadine, dimethyl dicarbonate, and/or 3-iodo-2-propinyl n-butylcarbamate.

Furthermore, highly active mixtures are also prepared with the following active ingredients:

Fungicides:

acypetacs, 2-aminobutane, ampropylfos, anilazine, benalaxyl, bupirimate, quinomethionate, chloroneb, chlozolinate, cymoxanil, dazomet, diclomezine, dichloram, diethofencarb, dimethirimol, diocab, dithianon, dodine, drazoxolon, edifenphos, ethirimol, etridiazole, fenarimol, fenitropan, fentin acetate, fentin hydroxide, ferimzone, fluazinam, fluromide, flusulfamide, flutriafol, fosetyl, fthalide, furalaxyl, guazatine, hymexazol, iprobenfos, iprodione, isoprothiolane, metalaxyl, methasulfocarb, nitrothal-isopropyl, nuarimol, ofurace, oxadiyl, perflurazoate, pencycuron, phosdiphen, pimaricin, piperalin, procymidone, propamocarb, propineb, pyrazophos, pyrifenox, pyroquilone, quintozene, tar oils, tecnazene, thicyofen, thiophanate-methyl, tolclofos-methyl, triazoxide, trichlamide, tricyclazole, triforine, vinclozolin.

Insecticides:

phosphoric esters such as azinphos-ethyl, azinphos-methyl, α-1(4-chlorophenyl)-4-(O-ethyl, S-propyl)-phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulfprofos, triazophos and trichlorphon;

Carbamates such as aldicarb, bendiocarb, α-2-(1-methylpropyl)-phenylmethylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

Organosilicon compounds, preferablydimethyl(phenyl)silyl-methyl 3-phenoxybenzyl ethers such as dimethyl-(4-ethoxyphenyl)-silylmethyl 3-phenoxybenzyl ether or (dimethylphenyl)-silyl-methyl-2-phenoxy-6-pyridyl methyl etherssuchas, for example, dimethyl-(9-ethoxyphenyl)-silylmethyl-2-phenoxy-6-pyridyl methyl ether or [(phenyl)-3-(3-phenoxyphenyl)-propyl](dimethyl)-silanes such as, for example, (4-ethoxyphenyl)-[3-(4-fluoro-3-phenoxyphenyl-propyl]dimethyl-silane, silafluofen;

Pyrethroids such as allethrin, alphamethrin, bioresmethrin, byfenthrin, cycloprothrin, cyfluthrin, decamethrin, cyhalothrin, cypermethrin, deltamethrin, alphacyano-3-phenyl-2-methylbenzyl 2,2-dimethyl-3-(2-chloro-2-trifluoro-methylvinyl)-cyclopropanecarboxylate fenpropathrin, fenfluthrin, fenvalerate, flucythrinate, flumethrin, fluvalinate, permethrin, resmethrin and tralomethrin;

Nitroimines and nitromethylenes such as 1-[(6-chloro-3-pyridinyl)-methyl]-4,5-dihydro-N-nitro-1H-imidazole-2-amine (imidacloprid), N-[(6-chloro-3-pyridyl)methyl-]N²-cyano-N¹-methylacetamide (NI-25);

abamectin, AC 303, 630, acephate, acrinathrin, alanycarb, aldoxycarb, aldrin, amitraz, azamethiphos, Bacillus thuringiensis, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, 0-2-tert.-butyl-pyrimidin-5-yl-o-isopropyl-phosphorothiate, thiocyclam, thiofanox, thiometon, tralomethrin, triflumuron, trimethacarb, vamidothion, Verticillium Lacanii, XMC, xylylcarb, benfuracarb, bensultap, bifenthrin, bioallethrin, MERbioallethrin (S)cyclopentenyl isomer, bromophos, bromophos-ethyl, buprofezin, cadusafos, calcium polysulfide, carbophenothion, cartap, quinomethionate, chlordane, chlorfenvinphos, chlorfluazuron, chlormephos, chlorpicrin, chlorpyrifos, cyanophos, beta-cyfluthrin, alpha-cypermethrin, cyophenothrin, cyromazine, dazomet, DDT, demeton-S-methylsulphon, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocar'b, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous, chloride, metam, Metarthizium, anisopliae, methacrifos, methamidophos, methidathion, methiocarb, methoprene, methoxychlor, methyl isothiocyanate, metholcarb, mevinphos, monocrotophos, naled, Neodiprion sertifer NPV, nicotine, omethoate, oxydemeton-methyl, pentachlorophenol, petroleum oils, phenothrin, phenthoate, phorate;

Molluscicides:

fentin acetate, metaldehyde, methiocarb. niclosamide, thiodicarb, trimethacarb;

Algicides:

copper sulphate, dichlororphen, endothal, fentin acetate, quinoclamine;

Herbicides:

| | |
|---|---|
| acetochlor | benzofencap |
| acifluorfen | benzthiazuron |
| aclonifen | bifenox |
| acrolein | bilanafos |
| alachlor | borax |
| alloxydim | bromacil |
| ametryn | bromobutide |
| amidosulfuron | bromofenoxim |
| amitrole | bromoxynil |
| ammonium sulphate | butachlor |
| anilofos | butamifos |
| asulam | butenachlor |
| atrazine | butralin |
| aziprotryne | butylate |
| benazolin | carbetamide |
| benfluralin | CGA 184927 |
| benfuresate | chloramben |
| bensulfuron | chlorbromuron |
| bensulide | chlorbufam |
| bentazone | chlorflurenol |
| chloridazon | difenoxuron |
| chlorimuron | difenzoquat |
| chlormethoxyfen | diflufenican |
| chlornitrofen | dimefuron |
| chloroacetic acid | dimepiperate |
| achloropicrin | dimethachlor |
| chlorotoluron | dimethametryn |
| chloroxuron | dimethipin |
| chlorpropham | dimethylarsinic acid |
| chlorsulfuron | dinitramine |
| chlorthal | dinoseb acetate |
| chlorthiamid | dinoseb |
| cinmethylin | dinoseb |
| cinofulfuron | dinoseb acetate |
| clethodim | dinoterb |
| clomazone | diphenamid |
| clomeprop | dipropetryn |
| clopyralide | diquat |
| cyanamide | dithiopyr |
| cyanazine | diuron |
| cycloate | DNOC |
| cycloxydim | PPX-A788 |

| | |
|---|---|
| 2,4-D | DPX-E96361 |
| daimuron | DSMA |
| dalapon | eglinazine |
| dazomet | endothal |
| 2,4-DB | epsorcarb |
| desmedipham | EPTC |
| desmetryn | ethalfluralin |
| dicamba | ethidimuron |
| dichlobenil | ethofumesate |
| dichlorprop | fenoxaprop |
| dichlorprop-P | fenoxaprop-P |
| diclofop | fenuron |
| diethatyl | flamprop |
| flamprop-M | MCPA-thioethyl |
| flazasulfuron | MCPB |
| fluazifop | mecoprop |
| fluazifop-P | mecoprop-P |
| fluchloralin | mefenacet |
| flumeturon | mefluidide |
| fluorocgycofen | metam |
| fluoronitrofen | metamitron |
| flupropanate | metazachlor |
| flurenol | methabenzthiazuron |
| fluridone | methazole |
| flurochloridone | methoprotryne |
| fluroxypyr | methyldymron |
| fomosafen | methylisothiocyanate |
| fosamine | metobromuron |
| furyloxyfen | metolachlor |
| glufosinate | metoxuron |
| glyphosate | metribzin |
| haloxyfop | metsulfuron |
| hexazinone | molinate |
| imazamethabenz | monoalide |
| imazapyr | monolinuron |
| imazaquin | MSMA |
| imazethapyr | naproanilide |
| ioxynil | napropamide |
| isopropalin | naptalam |
| isoproturon | neburon |
| isouron | nicosulfuron |
| isoxaben | nipyraclofen |
| isoxapyrifop | norflurazon |
| lactofen | orbencarb |
| lenacil | oryzalin |
| linuron | oxadiazon |
| LS830556 | oxyfluorfen |
| MCPA | paraquat |
| pebulate | simetryn |
| pendimethalin | SMY 1500 |
| pentachlorophenol | sodium chlorate |
| pentanochlor | sulfometuron |
| petroleum oils | tar oils |
| phenmedipham | TCA |
| picloram | tebutam |
| piperophos | tebuthiuron |
| pretilachlor | terbacil |
| primisulfuron | terbumeton |
| prodiamine | terbuthylazine |
| proglinazine | terbutryn |
| prometon | thiazafluron |
| prometryn | thifensulfuron |
| propachlor | thiobencarb |
| propanil | thiocarbazil |
| propaquizafop | tioclorim |
| propazine | tralkoxydim |
| propham | tri-allate |
| propyzamide | triasulfuron |
| prosulfocarb | tribenzuron |
| pyrazolynate | triclopyr |
| pyrazosulfuron | tridiphane |
| pyrazoxyfen | trietazine |
| pyributicarb | trifluralin |
| pyridate | UBl-C4874 |
| quinclorac | vernolate |
| quinmerac | |
| quinoclamine | |
| quizalofop | |
| quzlzalofop-P | |
| S-23121 | | sethoxydim
sifuron
simazine

The weight ratios of the active ingredients in these combinations of active ingredients can be varied within relatively large ranges.

The combinations of active ingredients preferably obtain the active ingredient in an amount of from 0.1 to 99.9%, in particular from 1 to 75%, particularly preferably from 5 to 50%, the remainder up to 100% being made up by one or more of the abovementioned co-components.

The term emulsion paints refers to aqueous coating compositions which have been rendered alkaline and are based on polymer dispersions which act as binder. Polymer dispersions which are frequently used to produce emulsion paints contain, for example, polyacrylates, styrene acrylates, polyvinyl acetate, polyvinyl propionate and other polymers. The attached formulations A, B and C give information by way of example on the composition of emulsion paints.

Coats of emulsion paints become infested by fungus in a humid environment, for example in the tropics, but also in humid rooms, in the foodstuffs or textile industry, in bathing halls, saunas and similar facilities, within a few months; in other words, a large number of different types of fungus propagate on the coatings. Fungal infestation of the coatings can also be permanently prevented, however, by incorporating a suitable fungicide into the coating compositions, for example by dispersing it with the pigments. With regard to such paint fungicides for emulsion paints, the person skilled in the art places the following requirements on them:

broad spectrum of action virtually insoluble in water not volatile not discolouring not odour-polluting low toxicity/ecotoxicity The substances according to the invention meet these requirements to a high level. Thus for the first time paint fungicides are available which can be employed effectively and without problems in emulsion paints.

The examples which follow serve to illustrate the invention. The invention is not, however, limited to the examples.

For testing the mould resistance of emulsion paints, the following procedure is adopted:

The coating composition to be tested is painted onto both sides of a suitable substrate.

In order to obtain results approximating to those in practice, some of the test specimens are leached out with running water (24 h; 20° C.) before the test for mould resistance; others are treated with a current of hot fresh air (7 days; 40° C.).

The test specimens prepared in this way are placed on an agar nutrient medium. Test specimens and nutrient medium are contaminated with fungal spores. After storage at 29°±1° C. and from 80to 90% rel. atmospheric humidity for from 2 to weeks, the specimens are compared. The coating is permanently mould-resistant if the test specimen remains free from fungus or at most a slight infestation of the edge can be detected.

For the contamination, fungal spores of the following mould fungi are used, which are known as paint destroyers or are frequently encountered on coatings:

1. *Alternaria tenuis*
2. *Aspergillus flavus*
3. *Aspergillus niger*
4. *Aspergillus ustus*
5. *Cladosporium herbarum*
6. *Paecilomyces variotii*
7. *Penicillium citrinum*
8. *Aureobasidium pullulans*
9. *Stachybotrys atra Corda*

EXAMPLE 1

Coatings according to formulation A are mould-resistant after leaching out and wind tunnel exposure if they contain 0.6% N-cyclohexyl-benzothiophene-2-carboxamide S,S-dioxide or 1 to 2% benzothiophene-2-carboxanilide S,S-dioxide.

The coatings containing anilide, however, undergo yellow discoloration.

EXAMPLE 2

Coatings according to formulation B are mould-resistant after leaching out and wind tunnel exposure if they contain 0.3 to 0.6% N-cyclohexyl-benzothiophene-2-carboxamide S,S-dioxide or 0.6 to 1.0% N-n-hexyl-benzothiophene-2-carboxamide S,S-dioxide or 1.0% N-n-butyl-benzothiophene-2-carboxamide S,S-dioxide.

The coatings containing anilide, however, undergo yellow discoloration.

EXAMPLE 3

Coatings according to formulation C are mould-resistant after leaching out and wind tunnel exposure if they contain 0.3 to 0.6% N-cyclohexyl-benzothiophene-2-carboxamide S,S-dioxide or 0.6% N-n-hexyl-benzothiophene-2-carboxamide S,S-dioxide.

FORMULATION A:
EXTERIOR emulsion paint based on Acronal 290 D
(styrene acrylate)

| Trade name | Parts by weight | Chemical name |
|---|---|---|
| Bayer Titan RKB2 | 40 | titanium dioxide |
| Talkum V58 neu | 10 | magnesium silicate, water-containing |
| Durcal 5 | 45 | calcite CaCO$_3$ |
| Walsroder MC 3000 S 2% strength | 30 | methylcellulose |
| H$_2$O | 6.5 | distilled water |
| Calgon N 10% strength | 3 | polyphosphate |
| Pigmentverteiler A 10% strength | 1 | polyacrylic acid salt |
| Agitan 281, 1:1 in Texanol | 1 | |
| Testbenzin | 5 | various aliphatic hydrocarbons |
| Butylglycol acetate | 1.5 | butylglycol acetate |
| Acronal 290 D (binder) | 71 | polyacrylic ester |
| Total | 219.0 | |

Solids content: 135.5 = 61.6%

FORMULATION B:
EXTERIOR emulsion paint based on Mowilith DM 2H
(polyvinyl acetate)

| Trade name | Parts by weight | Chemical name |
|---|---|---|
| Bayer Titan RKB2 | 35 | titanium dioxide |
| EWO-Pulver | 20 | heavy spar (BaSO$_4$) |
| Micro-Mica | 15 | magnesium aluminium silicate |
| Talkum | 5 | magnesium silicate, water-containing |
| Kreide BLP2 | 25 | calcite (CaCO$_3$) |
| Mowilith DM 2H (binder) | 80 | polyvinyl acetate |
| Tylose MH 2000 K | 20 | methylhydroxyethylcellulose |
| Calgon N 10% strength | 2.5 | polyphosphate |
| Pigmentverteiler A 10% strength | 2.5 | polyacrylic acid salt |
| H$_2$O | 5.0 | distilled water |
| Total | 210.0 | |

Solids content: 140 = 66%

FORMULATION C:
EXTERIOR emulsion paint based on Propiofan 590 D
(polyvinyl propionate)

| Trade name | Parts by weight | Chemical name |
|---|---|---|
| Bayer Titan RKB2 | 35 | titanium dioxide |
| EWO-Pulver | 10 | heavy spar (BaSO$_4$) |
| Micro-Mica | 10 | magnesium aluminium silicate |
| Talkum AT 1 | 5 | magnesium silicate, water-containing |
| Kreide BLP2 | 15 | calcite (CaCO$_3$) |
| Blanc fix | 25 | heavy spar (BaSO$_4$), synthetic |
| Propiofan 590 D (binder) | 50 | polyvinyl propionate |
| Tylose MH 2000 K | 20 | methylhydroxyethylcellulose |
| Calgon N 10% strength | 2.5 | polyphosphate |
| Pigmentverteiler A 10% strength | 2.5 | polyacrylic acid salt |
| H$_2$O | 3.0 | distilled water |
| Total | 178.0 | |

Solids content: 125 = 70%

We claim:

1. An emulsion paint comprising a fungicidally effective amount of N-cyclohexyl-benzothiophene-2-carboxamide S,S-dioxide.

* * * * *